United States Patent
Yamada et al.

(10) Patent No.: US 11,136,375 B2
(45) Date of Patent: *Oct. 5, 2021

(54) METHOD FOR PRODUCTION OF ANTIBODY

(71) Applicant: Chugai Seiyaku Kabushiki Kaisha, Tokyo (JP)

(72) Inventors: Yoshiki Yamada, Tokyo (JP); Tatsuya Kiyasu, Tokyo (JP); Kazuyuki Tabata, Tokyo (JP); Akihiro Kuzumaki, Tokyo (JP); Mai Yamashiro, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 278 days.

This patent is subject to a terminal disclaimer.

(21) Appl. No.: 15/589,000

(22) Filed: May 8, 2017

(65) Prior Publication Data

US 2017/0275351 A1 Sep. 28, 2017

Related U.S. Application Data

(62) Division of application No. 12/734,094, filed as application No. PCT/JP2008/068588 on Oct. 14, 2008, now Pat. No. 9,683,027.

(30) Foreign Application Priority Data

Oct. 15, 2007 (JP) .............................. JP2007-267384
Apr. 11, 2008 (JP) .............................. JP2008-103308

(51) Int. Cl.
 *C07K 16/00* (2006.01)
(52) U.S. Cl.
 CPC .......... *C07K 16/00* (2013.01); *C07K 2317/56* (2013.01); *C12N 2510/02* (2013.01)
(58) Field of Classification Search
 None
 See application file for complete search history.

(56) References Cited

U.S. PATENT DOCUMENTS

| | | | |
|---|---|---|---|
| 5,561,053 A † | 10/1996 | Crowley | |
| 5,795,965 A | 8/1998 | Tsuchiya et al. | |
| 6,171,586 B1 | 1/2001 | Lam | |
| 9,683,027 B2 * | 6/2017 | Yamada .................. | C07K 16/00 |
| 2002/0062010 A1 | 5/2002 | Arathoon et al. | |
| 2003/0010447 A1 | 1/2003 | Tzu | |
| 2003/0157641 A1 | 8/2003 | Reff et al. | |
| 2007/0065912 A1 | 3/2007 | Carson | |
| 2007/0178552 A1 † | 8/2007 | Arathoon | |
| 2007/0190599 A1 | 8/2007 | Nakano et al. | |

FOREIGN PATENT DOCUMENTS

| | | |
|---|---|---|
| EP | 1 652 925 A1 | 5/2006 |
| WO | WO 92/19759 A1 | 11/1992 |
| WO | WO-03/048306 A2 | 6/2003 |
| WO | WO 2006/006693 A1 | 1/2006 |
| WO | WO 2006/054063 A1 | 5/2006 |

OTHER PUBLICATIONS

Belyaev et al., "High-level expression of five foreign genes by a single recombinant baculovirus," Gene, 1995, 156:229-233.
Bibila, T., "A Structured Model for Monoclonal Antibody Synthesis in Exponentially Growing and Stationary Phase Hybridoma Cells," Biotechnology and Bioengineering, 1991, 37:210-226.
Bielekova, Bibiana, "Daclizumab Therapy for Multiple Sclerosis," Neurotherapeutics, 2013, 10:55-67.
Borth et al., "Analysis of changes during subclone development and ageing of human antibody-producing heterohybridoma cells by Northern blot and flow cytometry," Journal of Biotechnology, 1999, 67:57-66.
Communication of Notice of Opposition, Jun. 1, 2015, in EP 08838661.0, by Guenter Soelch, 15 pages.
Communication of Notice of Opposition, May 21, 2015, in EP 08838661.0, by Lonza AG, 35 pages.
Cregg et al., "Recent Advances in the Expression of Foreign Genes in *Pichia pastoris*," Bio/Technology, Aug. 1993, 11:905-910.
Dorai et al., "Correlation of Heavy and Light Chain mRNA Copy Numbers to Antibody Productivity in Mouse Myeloma Production Cell Lines," Hybridoma, 2006, 25(1):1-9.
Idusogie et al., "Mapping of the C1q Binding Site on Rituxan, a Chimeric Antibody with a Human IgG1 Fc," The Journal of Immunology, 2000, 164:4178-4184.
International Search Report dated Dec. 22, 2008, in PCT/JP2008/068588, 6 pages.
Jiang et al., "Regulation of Recombinant Monoclonal Antibody Production in Chinese Hamster Ovary Cells: A Comparative Study of Gene Copy Number, mRNA Level, and Protein Expression," Biotechnol. Prog., 2006, 22:313-318.
Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.
Kim et al "Characterization of Chimeric Antibody Producing CHO Cells in the Course of Dihydrofolate Reductase-Mediated Gene Amplification and Their Stability in the Absence of Selective Pressure," Biotechnol. Bioeng., 1998, 58:73-84.

(Continued)

*Primary Examiner* — Yunsoo Kim
(74) *Attorney, Agent, or Firm* — Foley & Lardner LLP

(57) ABSTRACT

The present invention provides a method of producing a recombinant antibody efficiently and at low cost. Disclosed is a method of producing an antibody or a fragment thereof, comprising allowing a cell to produce the antibody or the fragment, wherein the cell contains a larger number of copies of an exogenous DNA encoding the light chain or a fragment thereof of the antibody than the number of copies contained in the cell of an exogenous DNA encoding the heavy chain or a fragment thereof of the antibody. The present invention also provides a recombinant vector comprising one copy of a DNA encoding the heavy chain or a fragment thereof of an antibody and two or more copies of a DNA encoding the light chain or a fragment thereof of the antibody; and a transformant.

13 Claims, 4 Drawing Sheets

Specification includes a Sequence Listing.

(56) References Cited

OTHER PUBLICATIONS

Kim et al., "Decreased Chimeric Antibody Productivity of KR12H-1 Transfectoma During Long-Term Culture Results from Decreased Antibody Gene Copy Number," Biotechnology and Bioengineering, 1996, 51:479-487.

Kim et al., "Decreased Chimeric Antibody Productivity of KR12H-1 Transfectoma During Long-Term Culture Results from Decreased Antibody Gene Copy Number," Biotechnol. Bioeng., 1996, 51:479-487.

Kolb et al., "A virus-neutralising antibody is not cytotoxic in vitro," Molecular Immunology, 2006, 43:677-689.

Lee et al., "BiP and Immunoglobulin Light Chain Cooperate to Control the Folding of Heavy Chain and Ensure the Fidelity of Immunoglobulin Assembly," Molecular Biology of the Cell, Jul. 1999, 10:2209-2219.

Li et al., "A comparative study of different vector designs for the mammalian expression of recombinant IgG antibodies," Journal of Immunological Methods, 2007, 318:113-124.

Li et al., "Analysis of IgG heavy chain to light chain ratio with mutant Encephalomyocarditis virus internal ribosome entry site," Protein Engineering, Design & Selection, 2007, 20(10):491-496.

Mansur et al., "Multiple gene copy number enhances insulin precursor secretion in the yeast *Pichia pastoris*," Biotechnology Letters, 2005, 27:339-345.

Norderhaug et al., "Versatile vectors for transient and stable expression of recombinant antibody molecules in mammalian cells," Journal of Immunological Methods, 1997, 204:77-87.

Reff et al., "Depletion of B Cells In Vivo by a Chimeric Mouse Human Monoclonal Antibody to CD20," Blood, Jan. 15, 1994, 83(2):435-445.

Roy et al., "Baculovirus multigene expression vectors and their use for understanding the assembly process of architecturally complex virus particles," Gene, 1997, 190:119-129.

Schlatter et al., "On the Optimal Ratio of Heavy to Light Chain Genes for Efficient Recombinant Antibody Production by CHO Cells," Biotechnol. Prog., 2005, 21:122-133.

Schlatter et al., "On the Optimal Ratio of Heavy to Light Chain Genes for Efficient Recombinant Antibody Production by CHO Cells," Biotechnology, 2005, 21:122-133.

Svenson et al., "Monitoring patients treated with anti-TNF-α biopharmaceuticals: assessing serum infliximab and anti-infliximab antibodies," Rheumatology, 2007, 46:1828-1834.

Third Party Observations dated Feb. 4, 2013, in EP 08838661.0.

Vassileva et al., "Expression of hepatitis B surface antigen in the methylotrophic yeast *Pichia pastoris* using the *GAP* promoter," Journal of Biotechnology, 2001, 88:21-35.

Vincenzi et al., "CETUXIMAB: From Bench to Bedside," Current Cancer Drug Targets, 2010, 10:1-16.

Wikipedia entry for Adalimumab in German, cited May 7, 2015.
Wikipedia entry for Alemtuzumab in German, cited May 7, 2015.
Wikipedia entry for Basiliximab in German, cited May 7, 2015.
Wikipedia entry for Bevacizumab in German, cited May 7, 2015.
Wikipedia entry for Ibritumomab tiuxetan in German, cited May 7, 2015.
Wikipedia entry for Palivizumab in German, cited May 7, 2015.

Nehlsen et al., "Recombinant protein expression by targeting pre-selected chromosomal loci," BMC Biotechnology, Dec. 14, 2009, 9:100, 12 pages.

Wang et al., "Potential aggregation prone regions in biotherapeutics," mAbs, 2009, 1:254-267.

Smales et al., Biotech Bioeng 88: 474-488 (2004).†
Kalwy et al. (Mol. Biotech. 34: 151-156, 2006).†

\* cited by examiner
† cited by third party

US 11,136,375 B2

METHOD FOR PRODUCTION OF ANTIBODY

CROSS-REFERENCE TO RELATED APPLICATIONS

This application is a Divisional of U.S. application Ser. No. 12/734,094, which is the U.S. National Stage application of PCT/JP2008/068588, filed Oct. 14, 2008, which claims priority from Japanese application nos. JP 2007-267384, filed Oct. 15, 2007, and JP 2008-103308, filed Apr. 11, 2008.

The instant application contains a Sequence Listing which has been submitted in ASCII format via EFS-WEB and is hereby incorporated by reference in its entirety. Said ASCII copy, created on Apr. 17, 2017, is named sequence.txt and is 1 KB.

TECHNICAL FIELD

The present invention relates to a method of producing an antibody.

BACKGROUND ART

In the production of recombinant antibodies useful as pharmaceuticals by using genetic recombinant technology, use of animal cells enables complicated post-translational modification and folding which prokaryotic cells are unable to perform. Therefore, animal cells have been frequently used as host cells for producing recombinant antibodies.

Recently, a great number of biological pharmaceuticals, such as antibodies and physiologically active proteins, have been produced. In particular, in antibody preparations where doses are usually on the order of milligram (mg) per administration, considerable amounts of antibodies are needed as active ingredients. Technologies that allow efficient production of recombinant antibodies by animal cells will lead to cost reduction of antibody preparations and promise stable supply to patients.

Therefore, more efficient methods of producing recombinant antibodies are desired.

In the preparation of a host cell for producing a recombinant antibody, one copy of a DNA encoding the heavy chain of the antibody and one copy of a DNA encoding the light chain of the antibody are usually transferred into the host cell (Non-Patent Documents Nos. 1 and 2).

[Non-Patent Document No. 1] Reff M E, Caner K, Chambers K S, Chinn P C, Leonard J E, Raab R et al. Depletion of B cells in vivo by a chimeric mouse human monoclonal antibody to CD20. Blood. 1994 Jan. 15; 83(2):435-45.

[Non-Patent Document No. 2] Presta L G, Chen H, O'Connor S J, Chisholm V, Meng Y G, Krummen L, et al. Humanization of an anti-vascular endothelial growth factor monoclonal antibody for the therapy of solid tumors and other disorders. Cancer Res. 1997 Oct. 15; 57(20): 4593-9.

DISCLOSURE OF THE INVENTION

Problem for Solution by the Invention

On the other hand, it has not been known to date whether or not a transformed stable expression cell contributes to improvement of the production of a desired recombinant antibody when one copy of a DNA encoding the heavy chain of the antibody and two or more copies of a DNA encoding the light chain of the antibody have been transferred thereinto.

It is an object of the present invention to provide a method for high production of an antibody.

Means to Solve the Problem

As a result of intensive and extensive researches toward solution of the above problem, the present inventors have found it possible to increase antibody yields by using a cell containing a larger number of copies of an exogenous DNA encoding the light chain of an antibody of interest than the number of copies of an exogenous DNA encoding the heavy chain of the antibody it contains. Thus, the present invention has been achieved.

The present invention relates to the following.

(1) A method of producing an antibody or a fragment thereof, comprising allowing a cell to produce the antibody or the fragment, wherein the cell contains a larger number of copies of an exogenous DNA encoding the light chain or a fragment thereof of the antibody than the number of copies contained in the cell of an exogenous DNA encoding the heavy chain or a fragment thereof of the antibody.

(2) The method according to (1) above, wherein the cell containing a larger number of copies of an exogenous DNA encoding the light chain or a fragment thereof of the antibody than the number of copies contained in the cell of an exogenous DNA encoding the heavy chain or a fragment thereof of the antibody is a cell into which a vector comprising one copy of a DNA encoding the heavy chain or a fragment thereof of the antibody and two or more copies of a DNA encoding the light chain or a fragment thereof of the antibody has been introduced.

(3) The method according to (2) above, wherein the cell is an animal cell.

(4) The method according to (3) above, wherein the cell is Chinese hamster ovary cell.

(5) The method according to any one of (1) to (4) above, wherein the antibody is a chimeric antibody, humanized antibody or human antibody.

(6) The method according to any one of (1) to (5) above, wherein the antibody is selected from the group consisting of anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody and anti-VLA4 antibody.

(7) A method of manufacturing pharmaceuticals comprising the antibody or the fragment thereof prepared by the method according to any one of (1) to (6) above.

(8) A recombinant vector comprising one copy of a DNA encoding the heavy chain or a fragment thereof of an antibody and two or more copies of a DNA encoding the light chain or a fragment thereof of the antibody.

(9) A cell into which the vector according to (8) above has been introduced.

(10) A cultured cell containing a larger number of copies of an exogenous DNA encoding the light chain or a fragment thereof of an antibody than the number of copies contained in the cell of an exogenous DNA encoding the heavy chain or a fragment thereof of the antibody.

(11) A method of producing an antibody or a fragment thereof, comprising allowing a cell to produce the antibody or the fragment, said cell expressing the light chain or a fragment thereof of the antibody in higher yield than the heavy chain or a fragment thereof of the antibody.

(12) The method according to any one of (1) to (7) and (11) above, wherein the cell is stably expressing the antibody or the fragment thereof.

(13) The cell according to (9) or (10) above, which is stably expressing the antibody or the fragment thereof.

Effect of the Invention

According to the present invention, it has become possible to produce a desired recombinant antibody at low cost.

The present invention encompasses the contents disclosed in the specification and/or the drawings of Japanese Patent Application No. 2008-103308 based on which the present patent application claims priority.

BEST MODE FOR CARRYING OUT THE INVENTION

Figure 1:
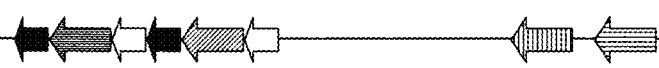
FIG. 1 shows "L-chain 1 copy expression plasmid" phGC33CAG#1 harboring one copy of light chain expression unit and one copy of heavy chain expression unit per plasmid, and "L-chain 2 copies expression plasmid" phGC33CAG1 harboring two copies of light chain expression unit and one copy of heavy chain expression unit per plasmid.
Figure 1:
Figure 1:
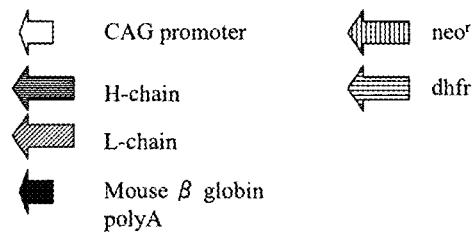

Hereinbelow, embodiments of the present invention will be described in detail.

The present invention provides a method of producing an antibody or a fragment thereof, comprising allowing a cell to produce the antibody or the fragment, wherein the cell contains a larger number of copies of an exogenous DNA encoding the light chain of the antibody or a fragment thereof than the number of copies contained in the cell of an exogenous DNA encoding the heavy chain or a fragment thereof of the antibody.

In the method of the present invention, a cell which contains a larger number of copies of an exogenous DNA encoding the light chain or a fragment thereof of an antibody than the number of copies contained in the cell of an exogenous DNA encoding the heavy chain or a fragment thereof of the antibody may be, for example, a transformed cell into which one copy of a DNA encoding the heavy chain or a fragment thereof of a desired recombinant antibody and two or more copies of a DNA encoding the light chain or a fragment thereof of the desired recombinant antibody have been introduced and which is capable of producing the desired recombinant antibody or a fragment thereof.

In the method of the present invention, the desired recombinant antibody is not particularly limited and may be a recombinant antibody to any antigen, e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody or the like. The antibody includes not only monoclonal antibodies derived from animals such as human, mouse, rat, hamster, rabbit and monkey, but also artificially modified gene recombinant antibodies such as chimeric antibodies, humanized antibodies, bispecific antibodies or the like. The recombinant antibody may be chemically modified, e.g., may be linked to various molecules such as polyethylene glycol. The class of the antibody is not particularly limited. The immunoglobulin class of the antibody is not particularly limited, and may be IgG (such as IgG1, IgG2, IgG3 or IgG4), IgA, IgD, IgE, IgM or the like. When the antibody is to be used as a pharmaceutical, IgG or IgM is preferable.

A DNA encoding the light chain of an antibody and a DNA encoding the heavy chain of the antibody may be prepared as described below. Briefly, mRNA is extracted from a hybridoma, cell, phage, ribosome or the like that has a gene encoding the antibody. From the resultant mRNA, cDNA is prepared by reverse transcription using reverse transcriptase. The light chain gene or the heavy chain gene is amplified by PCR using the cDNA and primers having a nucleotide sequence complementary to the light chain or heavy chain gene. Each gene is obtained by ligating the PCR product into a cloning plasmid.

In the method of the present invention, specific examples of desirable fragments of recombinant antibodies include Fab, F(ab')2 and Fv.

A DNA encoding an light chain fragment of an antibody and a DNA encoding an heavy chain fragment of the antibody may be prepared as described below. Briefly, mRNA is extracted from a hybridoma, cell, phage, ribosome or the like that has a gene encoding the antibody. From the resultant mRNA, cDNA is prepared by reverse transcription using reverse transcriptase. The light chain fragment gene or the heavy chain fragment gene is amplified by PCR using the cDNA and primers having a nucleotide sequence complementary to the light chain fragment or heavy chain fragment gene. Each fragment gene is obtained by ligating the PCR product into a cloning plasmid.

The present inventors have found that use of a transformed cell into which one copy of a DNA encoding the heavy chain and two or more copies of a DNA encoding the light chain have been introduced increases the yield of a desired recombinant antibody definitely and significantly, compared to conventionally used transformed cells into which one copy of a DNA encoding the heavy chain and one copy of a DNA encoding the light chain have been introduced.

The heavy chain polypeptide and light chain polypeptide of an antibody molecule assemble with the support of BiP (immunoglobulin heavy chain binding protein) and then fold to thereby achieve a complete antibody structure. This assemble process is dependent on the light chain polypeptide (Molecular Biology of the Cell, 1999, 10, 2209). Therefore, it can be believed that by increasing the ratio of the number of the light chain gene to thereby raise the ratio of the light chain polypeptide, the assembling of heavy chain polypeptides and light chain polypeptides will be promoted and, as a result, antibody yield will be increased.

However, particularly in stable transformants which are expressing recombinant antibodies in stable expression systems, the expression level of heavy chain is lowered relative to the expression level in transient expression systems; thus, it is suggested that the expression level of heavy chain is more important here (Biotechnol. Prog., 2005, 21, 122). Therefore, it is completely unknown how to control the ratio of expression levels of the heavy chain and light chain of an antibody of interest in order to increase the antibody yield in stable expression systems.

The ratio of the number of copies of a DNA encoding the light chain or a fragment thereof of a recombinant antibody to the number of copies of a DNA encoding the heavy chain or a fragment thereof of the antibody may be 1 or more, preferably within a range from 1.1 to 5, most preferably 2.

As examples of the cell containing a larger number of copies of an exogenous DNA encoding the light chain or a fragment thereof of an antibody than the number of copies contained in the cell of an exogenous DNA encoding the heavy chain or a fragment thereof of the antibody, the following cells may be given: a cell into which a vector (say, one in number) comprising a DNA encoding the heavy chain or a fragment thereof and other vectors (say, two or more in number) comprising a DNA encoding the light chain or a fragment thereof have been introduced; a cell into which a vector comprising both one copy of a DNA encoding the heavy chain or a fragment thereof and one copy of a DNA encoding the light chain or a fragment thereof and one or more other vectors comprising one copy of a DNA encoding the light chain or a fragment thereof have been introduced; or a cell into which a vector comprising one copy of a DNA encoding the heavy chain or a fragment thereof and two or more copies of a DNA encoding the light chain or a fragment thereof has been introduced. Preferable is a cell into which a vector comprising one copy of a DNA encoding the heavy chain or a fragment thereof and two or more copies of a DNA encoding the light chain or a fragment thereof has been introduced.

When one copy of a DNA encoding the heavy chain or a fragment thereof and two or more copies of a DNA encoding the light chain or a fragment thereof are used and at least one of these copies is encoded on a separate vector other than the vector encoding the remaining copies, the order of introduction of vectors is not particularly limited. Such vectors may be introduced separately or simultaneously.

The cell which is used in the present invention for expressing an antibody of interest is not particularly limited and any cell may be used; e.g., a eukaryotic cell such as animal cell, plant cell or yeast, or a prokaryotic cell such as *Escherichia coli* or *Bacillus subtilis*. Preferable examples include, but are not limited to, such animal cells as CHO cell, COS cell, 3T3 cell, myeloma cell, BHK cell, HeLa cell and Vero cell. Especially preferable is CHO cell. Further, in order to produce a desired antibody, it is preferred that the cell is CHO dhfr– cell or the like which is suitable for introduction of a desired gene. For example, it is possible to culture a COS or CHO cell into which a gene encoding a desired antibody has been integrated by genetic engineering operations.

With respect to vectors which may be used in the method of the present invention, when the host cell is *E. coli*, the vector preferably has ori that enables large scale amplification in *E. coli* (e.g., JM109, DH5α, HB101 and XL1-Blue) and selective markers for transformed *E. coli* cells (e.g., drug resistance genes capable of selecting transformants with drugs such as ampicillin, tetracycline, kanamycin or chloramphenicol). Specific examples of vectors include, but are not limited to, M13 vector, pUC vector, pBR322, pBluescript and pCR-Script. Further, when subcloning and excision of cDNA are intended, pGEM-T, pDIRECT, pT7 and the like are also enumerated in addition to the above-listed vectors. When the vector is used for the purpose of producing the antibody of the present invention or a fragment thereof, expression vectors are particularly useful. When the antibody of the present invention is to be expressed in *E. coli*, it is preferred that the expression vector has the above-described feature to enable amplification in *E. coli*. Furthermore, when the host is *E. coli* such as JM109, DH5α, HB101 or XL1-Blue, it is preferred that the expression vector has a promoter which enables efficient expression in *E. coli*, e.g., lacZ promoter (Ward et al, Nature (1989) 341, 544-546; FASEB J. (1992) 6, 2422-2427), araB promoter (Better et al., Science (1988) 240, 1041-1043) or T7 promoter. Specific examples of such vector include, in addition to those listed above, pGEX-5X-1 (Pharmacia), QIAexpress system (Qiagen) pEGFP or pET (in this case, the host cell is preferably BL21 that is expressing T7 RNA polymerase).

The vector may comprise a signal sequence for polypeptide secretion. As to the signal sequence for polypeptide secretion, pelB signal sequence (Lei, S. P. et al J. Bacteriol. (1987) 169, 4379) may be used when the antibody is to be produced in the periplasm of *E. coli*. Introduction of the vector into host cells may be performed by the calcium chloride method, electroporation, etc.

When the host cell is not *E. coli*, the vector which may be used in the present invention include, but are not limited to, mammal-derived expression vectors such as pcDNA3 (Invitrogen), pEGF-BOS (Nucleic Acids. Res. 1990, 18(17), p. 5322), pEF, pCDM8 and INPEP4 (Biogen-IDEC); insect cell-derived expression vectors such as Bac-to-BAC baculovairus expression system (GIBCO BRL) and pBacPAK8; plant-derived expression vectors such as pMH1 and pMN2; animal virus-derived expression vectors such as pHSV, pMV and pAdexLcw; retrovirus-derived expression vectors such as pZIpneo; yeast-derived expression vectors such as *Pichia* Expression Kit (Invitrogen), pNV11 and SP-Q01) and *B. subtilis*-derived expression vectors such as pPL608 and pKTH50.

When expression of an antibody in an animal cell (such as CHO cell, COS cell or NIH3T3 cell) is intended, the vector preferably has a promoter necessary for intracellular expression of the antibody; e.g., SV40 promoter (Mulligan et al., Nature (1979) 277, 108), MMLV-LTR promoter, EF1α promoter (Mizushima et al., Nucleic Acids Res. (1990) 18, 5322), CMV promoter (Niwa et al., Gene. (1991) 108, 193), mouse β globin promoter (mBGP), etc. More preferably, the vector has genes for selecting transformation into cells (e.g., drug resistance genes capable of selection with drugs such as neomycin or G418). Examples of vectors with such features include, but are not limited to, pMAM, pDR2, pBK-RSV, pBK-CMV, pOPRSV and pOP13. It is known that mRNA with polyA is stable within cells. Thus, the vector preferably has a polyA signal necessary to add polyA to a gene of interest, e.g., mouse β globin polyA signal, bovine growth hormone polyA signal, SV40 polyA signal, etc.

The cell of the present invention may be expressing the antibody or a fragment thereof either in a transient expression system or in a stable expression system. Preferably, the antibody is expressed in a stable expression system.

The "transient expression system" means a method in which circular plasmids are taken into cells by the calcium phosphate method, electroporation, lipofection, etc. for the purpose of gene expression. Since circular plasmids are inserted into chromosomes at low efficiency, the gene of interest often remains outside of chromosomes. Therefore, it is difficult to retain the expression of the gene of interest from circular plasmids for a long time.

The "stable expression system" means a method in which linear plasmids prepared by restriction enzyme treatment or the like are taken into cells by the calcium phosphate method, electroporation, lipofection, etc. for the purpose of gene expression. Since linear plasmids are inserted into chromosomes at higher efficiency than circular plasmids, the gene of interest is maintained on chromosomes at higher efficiency. Therefore, it is possible to retain the expression of this gene for a long time. Further, introduction of drug resistance genes into plasmids enables selection with drugs. Thus, it becomes possible to efficiently select those cells maintaining the gene of interest on their chromosomes. As animal cells used in a stable expression system, CHO cell, NS0 cell, SP2/0 cell and the like may be enumerated. Preferably, CHO cell is used.

Further, when stable expression of the gene of interest and intracellular amplification of the copy number of the gene are intended, a method may be given in which a nucleic acid synthesis pathway-deficient CHO cell is used. Briefly, a vector comprising a DHFR gene complementing the deficiency (e.g., pCHOI) is introduced into the cell, followed by amplification of the gene of interest with methotrexate (MTX). When transient expression of a gene of interest is intended, a method may be given in which a COS cell having a gene expressing SV40 T antigen on its chromosome is transformed with a vector having a replication origin for SV40 (e.g., pcD). As the replication origin, those derived from polyomavirus, adenovirus, bovine papillomavirus (BPV) and the like may also be used. Further, for amplification of the copy number of the gene of interest in host cell systems, expression vectors may comprise, the following as selective markers: aminoglycoside transferase (APH) gene, thymidine kinase (TK) gene, *E. coli* xanthine-guanine phosphoribosyl transferase (Ecogpt) gene, dihydrofolate reductase (dhfr) gene, etc.

The present invention also provides a recombinant vector comprising one copy of a DNA encoding the heavy chain or a fragment thereof of an antibody and two or more copies of a DNA encoding the light chain or a fragment thereof of the antibody.

The vector of the present invention is useful in retaining a DNA encoding a recombinant antibody of interest or a fragment thereof or expressing the recombinant antibody or the fragment thereof in a host cell. By introducing into the host cell one copy of a DNA encoding the heavy chain or a fragment thereof of the recombinant antibody and two or more copies of a DNA encoding the light chain or a fragment thereof of the recombinant antibody, assembling of the heavy chain polypeptide into an antibody molecule is promoted. Thus, production of the recombinant antibody of interest or a fragment thereof by the host cell can be increased.

The present invention also provides a host cell into which the vector of the present invention has been introduced. The host cell into which the vector of the present invention is to be introduced is not particularly limited. For example, *E. coli* or various animal cells may be used. The host cell of the present invention may be used as a production system for preparing or expressing the antibody of the present invention or a fragment thereof. As a production system for polypeptides, an in vitro or in vivo production system may be used.

Examples of in vitro production systems include those using eukaryotic cells and those using prokaryotic cells.

When eukaryotic cells are to be used, animal cells, plant cells or fungal cells may be used as the host. Specific examples of animal cells include, but are not limited to, mammal cells such as CHO (J. Exp. Med. (1995) 108, 945), COS, 3T3, myeloma, BHK (baby hamster kidney), HeLa and Vero cells; amphibian cells such as *Xenopus* oocyte (Valle, et al., Nature (1981) 291, 358-340) and insect cells such as Sf9, Sf21 and Tn5. With respect to CHO cells, a CHO cell lacking in DHFR gene (dhfr-CHO) (Proc. Natl. Acad. Sci. USA (1980) 77, 4216-4220) or CHO K-1 cell (Proc. Natl. Acad. Sci. USA (1968) 60, 1275) may be used conveniently. When mass expression is intended in animal cells, CHO cells are particularly preferable. Introduction of the vector into the host cell may be performed by the calcium phosphate method, the DEAE dextran method, a method using a cationic ribosome DOTAP (Boehringer Mannheim), electroporation, lipofection, etc.

With respect to plant cells, a *Nicotiana tabacum*-derived cell is known as a polypeptide production system and this may be callus-cultured. With respect to fungal cells, yeasts such as *Saccharomyces* (e.g., *Saccharomyces cerevisiae*) and filamentous fungi such as *Aspergillus* (e.g., *Aspergillus niger*) are known.

When prokaryotic cells are to be used, production systems using bacterial cells may be used. Known examples of such bacterial cells include *E. coli* (e.g., JM109, DH5α and HB101) and *B. subtilis*.

By transforming these cells with a gene of interest and culturing the resultant transformants in vitro, a polypeptide encoded by the gene of interest may be obtained. The culture may be performed according to known methods. For example, as a culture broth for animal cells, DMEM, MEM, RPMI1640 or IMDM may be used. During this culture, a serum supplement such as fetal calf serum (FCS) may be used jointly. Alternatively, the culture may be serum-free culture. The pH during the culture is preferably about 6-8. Usually, the culture is performed at about 30-40° C. for about 15-200 hours. The culture medium may be exchanged, aerated or stirred if necessary.

By culturing a cell containing a larger number of copies of an exogenous DNA encoding the light chain or a fragment thereof of an antibody of interest than the number of copies contained in the cell of an exogenous DNA encoding the heavy chain or a fragment thereof of the antibody, it is possible to allow this cell to express the antibody or a fragment thereof in higher yield than in conventional methods. For culturing the above-described cell, media used in conventional cell (preferably, animal cell) culture may be used. Usually, these media contain amino acids, vitamins, lipid factors, energy sources, osmotic regulators, iron sources and pH buffers. The amounts of these components in the culture medium are usually 0.05 to 1,500 mg/L for amino acids, 0.001 to 10 mg/L for vitamins, 0 to 200 mg/L for lipid factors, 1 to 20 g/L for energy sources, 0.1 to 10,000 mg/L for osmotic regulators, 0.1 to 500 mg/L for iron sources, 1 to 10,000 mg/L for pH buffers, 0.00001 to 200 mg/L for trace metal elements, 0 to 5,000 mg/L for surfactants, 0.05 to 10,000 μg/L for growth cofactors and 0.001 to 50 mg/L for nucleosides. However, their amounts are not limited to these ranges and may be determined appropriately depending on such factors as the type of the cell to be cultured and the type of the desired antibody or a fragment thereof.

In addition to the above-listed components, trace metal elements, surfactants, growth cofactors and nucleosides may also be added to the medium.

Specifically, culture media containing the following components may be given: amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$, and ascorbic acid, preferably, biotin, folic acid, lipoic acid, nicotinic acid amide, calcium pantothenate, pyridoxal hydrochloride, riboflavin, thiamine hydrochloride, vitamin $B_{12}$, and ascorbic acid; lipid factors, such as choline chloride, choline tartrate, linoleic acid, oleic acid, and cholesterol, preferably, choline chloride; energy sources, such as glucose, galactose, mannose and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH buffers, such as sodium hydrogen-carbonate, calcium chloride, sodium hydrogen-phosphate, HEPES, and MOPS, preferably, sodium dihydrogen-carbonate.

Besides the above-listed components, there may be added trace metal elements, such as copper sulfate, manganese sulfate, zinc sulfate, magnesium sulfate, nickel chloride, tin chloride, magnesium chloride, and sodium subsilicate, preferably, copper sulfate, zinc sulfate, and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid, and putrescine hydrochloride, preferably, sodium selenite, ethanolamine hydrochloride, recombinant IGF-1 and putrescine hydrochloride; and nucleosides, such as deoxyadenosine, deoxycytidine, deoxyguanosine, adenosine, cytidine, guanosine and uridine. In preferred examples of the above medium, antibiotics such as streptomycin, penicillin-G potassium and gentamicin and pH-indicators such as Phenol Red may be contained.

The pH of the medium differs with the cell to be cultured but a suitable range is generally pH 6.8 to 7.6, more often pH 7.0 to 7.4.

Alternatively, commercially available culture media for animal cell may also be used. For example, D-MEM (Dulbecco's Modified Eagle Medium), D-MEM/F-12 1:1 Mixture (Dulbecco's Modified Eagle Medium: Nutrient Mixture F-12), RPMI1640, CHO-S-SFM II (Invitrogen), CHO-SF (Sigma-Aldrich), EX-CELL 301 (JRH Biosciences), CD-CHO (Invitrogen), IS CHO-V (Irvine Scientific) and PF-ACF-CHO (Sigma-Aldrich) may be enumerated.

The medium may be a serum-free medium.

When the host cell is a CHO cell, the cell may be cultured by methods known to those skilled in the art. For example, the CHO cell may be cultured under an atmosphere with a $CO_2$ concentration of 0 to 40%, preferably 2 to 10%, at 30 to 39° C., preferably about 37° C.

The appropriate period of culture of the cell for producing a desired recombinant antibody or a fragment thereof is usually from one day to three months, preferably from one day to two months, and more preferably from one day to one month.

Culture may be performed using various culture devices for animal cell culture, for example, a fermentor type tank culture device, an air lift type culture device, a culture flask type culture device, a spinner flask type culture device, a microcarrier type culture device, a fluidized bed type culture device, a hollow fiber type culture device, a roller bottle type culture device, and a packed bed type culture device.

Culture may be performed by any method such as batch culture, fed-batch culture, continuous culture or the like. Preferable is fed-batch culture or continuous culture, and fed-batch culture is more preferable.

As regards in vivo systems for producing antibodies or fragments thereof, production systems using an animal or a plant may be given. A gene of interest is introduced into the animal or plant. Then, the animal or plant is allowed to produce a polypeptide of interest in its body, followed by recovery of the polypeptide. The term "host" used in the present invention includes such animals or plants.

When an animal is to be used, production systems are available using a mammal or an insect. Examples of mammals which may be used in the present invention include, but are not limited to, goat, pig, sheep, mouse and bovine (Vicki Glaser, SPECTRUM Biotechnology Applications, 1993). When a mammal is to be used, a transgenic animal may be employed.

Methods of preparing transgenic animals are known. For example, a transgenic animal may be obtained according to the method described in Proc. Natl. Acad. Sci. USA 77:7380-7384 (1980). Specifically, a gene of interest is introduced into totipotent cells of a mammal. These cells are allowed to develop into individuals. Those individuals in which the introduced gene has been integrated into somatic cells and germ cells are selected from the resultant individuals. Thus, the transgenic animal of interest can be prepared. As totipotent cells into which a gene of interest is to be introduced, not only fertilized eggs and early embryos but also cultured cells such as ES cell having multipotency may be mentioned.

For example, a gene of interest (in the present invention, a DNA encoding the heavy chain or a fragment thereof of an antibody and a DNA encoding the light chain or a fragment thereof of the antibody) may be prepared as a fusion gene, by fusing it with a gene encoding a polypeptide, such as goat β casein, specifically produced into milk. DNA fragments comprising this fusion gene are injected into goat embryos, which are then transplanted into female goats. The polypeptide of interest (in the present invention, an antibody or a fragment thereof) can be recovered from milk produced by the transgenic goats (born from the goats that had received the modified embryos) or by their offspring. In order to increase the amount of milk containing the polypeptide produced by the transgenic goats, appropriate hormones may be administered to them (Ebert et al., Bio/Technology (1994) 12, 699-702).

Alternatively, insects such as silkworm may be used. A gene encoding a polypeptide of interest (in the present invention, a DNA encoding the heavy chain or a fragment thereof of an antibody and a DNA encoding the light chain or a fragment thereof of the antibody) inserted into baculovirus may be used to transfect silkworms, and the polypeptide of interest may be recovered from the body fluid of the silkworms (Susumu et al., Nature (1985) 315, 592-594).

If a plant is to be used tobacco may be used. When tobacco is used, a gene encoding a polypeptide of interest (in the present invention, a DNA encoding the heavy chain or a fragment thereof of an antibody and a DNA encoding the light chain or a fragment thereof of the antibody) may be inserted into a plant expression vector, such as pMON 530, which is introduced into a bacterium, such as *Agrobacterium tumefaciens*. Then, this bacterium is used to transfect a tobacco plant, such as *Nicotiana tabacum*, and the polypeptide of interest (in the present invention, the antibody or a fragment thereof) is recovered from its leaves (Julian et al., Eur. J. Immunol. (1994) 24, 131-138).

The present invention also provides a cultured cell containing a larger number of copies of an exogenous DNA encoding the light chain or a fragment thereof of an antibody than the number of copies contained in the cell of an exogenous DNA encoding the heavy chain or a fragment thereof of the antibody. The cultured cell is as described above.

Further, the present invention provides a method of producing an antibody or a fragment thereof, comprising allowing a cell to produce the antibody or the fragment, said cell expressing the light chain or a fragment thereof of the antibody in higher yield than the heavy chain or a fragment thereof of the antibody. As an example of the cell expressing the light chain or a fragment thereof of an antibody in higher yield than the heavy chain or a fragment thereof of the antibody, a cell may be mentioned which contains a larger number of copies of an exogenous DNA encoding the light chain or a fragment thereof of the antibody than the number of copies contained in the cell of an exogenous DNA encoding the heavy chain or a fragment thereof of the antibody. Such a cell is as described above. By culturing a cell expressing the light chain or a fragment thereof of an antibody in higher yield than the heavy chain or a fragment thereof of the antibody, it is possible to allow the cell to produce the antibody or a fragment thereof. The culture medium and culture conditions are as described above.

The antibody produced by the production method of the present invention includes not only monoclonal antibodies derived from animals such as human, mouse, rat, hamster, rabbit and monkey, but also artificially modified gene recombinant antibodies such as chimeric antibodies, humanized antibodies and bispecific antibodies. The class of the antibody is not particularly limited. The immunoglobulin class of the antibody is not particularly limited, and may be IgG (such as IgG1, IgG2, IgG3 or IgG4), IgA, IgD, IgE, IgM or the like. When the antibody is to be used as a pharmaceutical, IgG or IgM is preferable. Further, the antibody of the present invention includes not only whole antibodies but also antibody fragments such as Fv, Fab, F(ab)$_2$, etc.

The antibody produced by the method of the present invention may be further linked to various molecules such as polyethylene glycol (PEG) and used as a modified antibody. Such a modified antibody may be obtained by chemically modifying the resultant antibody. Methods for such modification have already been established in the art.

The above-described antibody of the present invention may be prepared by methods well known to those skilled in the art.

Monoclonal antibody-producing hybridomas may be prepared basically by using known techniques, as described below. Briefly, a desired antigen or a cell expressing the desired antigen is used as a sensitizing antigen, followed by immunization of cells in accordance with conventional procedures. The resulting immunocytes are then fused to known parent cells using conventional procedures for cell fusion, followed by selection of monoclonal antibody-producing cells (hybridomas) through conventional screening procedures. Preparation of hybridomas may be performed according to, for example, the method of Milstein et al. (Kohler, G and Milstein, C., Methods Enzymol. (1981) 73:3-46). When the immunogenicity of the antigen used is low, the antigen may be conjugated with an immunogenic macromolecule (e.g., albumin) before use in immunization.

Further, antibody genes are cloned from hybridomas, integrated into appropriate vectors, and then transferred into hosts to thereby obtain gene recombinant antibodies produced with gene recombination technology (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNA of the variable domain (V domain) of an antibody of interest is synthesized from hybridoma mRNA using reverse transcriptase. Once a DNA encoding the V domain of the antibody of interest is obtained, the DNA is ligated to a DNA encoding the constant domain (C domain) of the antibody and integrated into an expression vector. Alternatively, the DNA encoding the antibody V domain may be integrated into an expression vector carrying the DNA encoding the antibody C domain. The DNA construct is integrated into an expression vector so that the DNA is expressed under the control of expression regulatory regions, e.g., an enhancer or a promoter. Host cells are then transformed with this expression vector for antibody expression.

In the present invention, it is possible to use gene recombinant antibodies (e.g., chimeric antibodies, humanized antibodies) that are artificially modified typically for the purpose of reducing heterologous antigenicity against human. These modified antibodies may be prepared by known methods. A chimeric antibody is composed of variable domains of heavy and light chains from a non-human mammalian (e.g., mouse) antibody and constant domains of heavy and light chains from a human antibody. Chimeric antibodies may be obtained by ligating DNAs encoding mouse antibody variable domains to DNAs encoding human antibody constant domains, integrating the resultant DNA construct into an expression vector, and transforming the vector into a host for antibody production.

Humanized antibodies are also called reshaped human antibodies and obtained by grafting the complementarity-determining regions (CDRs) of an antibody from a non-human mammal such as mouse into the complementarity-determining regions of a human antibody. General gene recombination techniques for preparing them are also known. Specifically, a DNA sequence designed to allow ligation of the CDRs of a mouse antibody to the framework regions (FRs) of a human antibody is synthesized by PCR from several oligonucleotides prepared to have sections overlapping with one another at the ends. The resultant DNA is ligated to a DNA encoding the human antibody constant domains and integrated into an expression vector, followed by transformation into a host for antibody production (see European Patent Publication No. EP 239400 and International Patent Publication No. WO 96/02576). The FRs of the human antibody linked through the CDRs are selected in such a manner that the complementarity-determining regions form an appropriate antigen-binding site. If necessary, reshaped humanized antibodies may have some amino acid changes in the framework regions of the variable regions so that the complementarity-determining regions form an appropriate antigen-binding site (Sato, K. et al., Cancer Res. (1993) 53, 851-856).

Procedures for obtaining human antibodies are also known. For example, human lymphocytes are sensitized in vitro with a desired antigen or a cell expressing the desired antigen, and the sensitized lymphocytes are then fused to human myeloma cells (e.g., U266) to yield a desired human antibody having binding activity to the antigen (see Japanese Patent Publication No. 01-59878). Alternatively, a transgenic animal having the entire repertorire of human antibody genes may be immunized with an antigen to obtain a desired human antibody (see International Publication Nos. WO 93/12227, WO 92/03918, WO 94/02602, WO 94/25585, WO 96/34096, and WO 96/33735). Methods for obtaining a human antibody by panning with a human antibody library are also known. For example, phages binding to an antigen can be selected by expressing the variable regions of a human antibody as single-chain antibody fragments (scFv) on phage surfaces by a phage display method. By analyzing the genes of the selected phages, it is possible to determine the DNA sequences encoding the variable regions of the human antibody binding to the antigen. Once the DNA sequences of the scFv fragments binding to the antigen are determined, it is possible to prepare an appropriate expression vector comprising the DNA sequence and obtain a human antibody. These methods are already well known and can be found in WO 92/01047, WO 92/20791, WO 93/06213, WO 93/11236, WO 93/19172, WO 95/01438 and WO 95/15388.

The antibody or a fragment thereof obtained as described above can be purified to homogeneity. Isolation and purification of the antibody or a fragment thereof may be performed by isolation/purification methods used for conventional polypeptides. For example, the antibody may be isolated and purified by appropriately selecting and combining chromatography columns (such as affinity chromatography), filters, ultrafiltration, salting out, dialysis, SDS polyacrylamide gel electrophoresis, isoelectric focusing, etc. (Antibodies: A Laboratory Manual. Ed Harlow and David Lane, Cold Spring Harbor Laboratory, 1988) but are not limited to those listed above. The concentration of the thus obtained antibody may be determined by measuring absorbance or by enzyme-linked immunosorbent assay (ELISA).

As columns to be used in affinity chromatography, protein A column and protein G column may be mentioned. Examples of protein A columns include Hyper D, POROS, and Sepharose F. F. (Pharmacia).

Chromatographies other than affinity chromatography include, for example, ion exchange chromatography, hydrophobic chromatography, gel filtration, reversed-phase chromatography, and adsorption chromatography (Strategies for Protein Purification and Characterization: A Laboratory Course Manual. Ed Daniel R. Marshak et al., Cold Spring Harbor Laboratory Press, 1996). These chromatographies may be performed in the form of liquid chromatography such as HPLC or FPLC.

It is also possible to treat the produced polypeptide with an appropriate polypeptide-modifying enzyme before or after it is purified, to thereby add a desired modification or to remove a peptide partially. Polypeptide-modifying enzymes include trypsin, chymotrypsin, lysyl endopeptidase, protein kinase, glucosidase, etc.

When the antibody or a fragment thereof produced by the method of the present invention has a biological activity applicable as pharmaceuticals, it is possible to prepare pharmaceuticals by mixing and formulating the polypeptide with pharmaceutically acceptable carriers or additives.

These pharmaceutically acceptable carriers or additives include, for example, water, pharmaceutically acceptable organic solvents, collagen, polyvinylalcohol, polyvinylpyrrolidone, carboxyvinylpolymer, sodium carboxylmethylcellulose, sodium polyacrylate, sodium alginate, water-soluble dextran, sodium carboxylmehylstarch, pectin, methylcellulose, ethylcellulose, xanthan gum, arabic gum, casein, agar, polyethylenglycol, diglycerol, glycerol, propylene glycol, petrolatum, paraffin, stearyl alcohol, stearic acid, human serum albumin (HSA), mannitol, sorbitol, lactose, [a]nd pharmaceutically acceptable surfactants.

The carries or additives may be selected alone or in a suitable combination from the above-listed substances depending on the dosage form of the pharmaceutical of the present invention. It should be taken for granted that the carriers or additives are not limited to those listed above. For example, when the polypeptide of the present invention is used as a preparation for injection, the purified polypeptide may be dissolved in a solvent (such as physiological saline, buffer or glucose solution), followed by addition to the solution of an absorption-inhibiting agent such as Tween80, Tween20, gelatin, or human serum albumin. Alternatively, the polypeptide of the present invention may be lyophilized to give a dosage form that can be dissolved for reconstitution before use. As excipients for lyophilization, sugar alcohols and sugars such as mannitol and glucose may be used.

The effective dose of the antibody or a fragment thereof is appropriately selected depending on the type of the antibody or a fragment thereof, the type of a disease to be treated or prevented, the age of the patient, the severity of the disease, etc. For example, when the antibody is anti-glypican-3 antibody and used as an anticancer agent, the effective dose of the antibody is selected within the range from 0.001 to 1000 mg/kg body weight per administration. Alternatively, a dose of 0.01 to 100,000 mg/body may be selected. However, the dose is not limited to these levels.

Administration of the antibody or a fragment thereof may be either oral or parenteral, but parenteral administration is preferable. Specifically, injection (systemic or local administration by intravenous, intramuscular, intraperitoneal or subcutaneous injection), nasal administration, pulmonary administration, transdermal administration, or the like may be enumerated.

EXAMPLES

Hereinbelow, the present invention will be described specifically with reference to Examples. It should be noted that these Examples are provided only for explaining the present invention and in no way limit the scope of the present invention.

[Example 1] Preparation of Humanized Anti-Human Glypican-3 Antibody Expression Plasmid First, the heavy chain gene of humanized anti-human glypican-3 antibody was prepared as described below. A glypican-3 fragment (obtained by expressing a GST-fusion protein gene by PCR) was used to immunize mice (MRL/lpr, Charles River Japan). Hybridoma cells were prepared using spleenocytes from these mice. Hybridoma cells were screened by ELISA using glypican-3 as antigen to thereby select those clones which produced glypican-3 binding antibodies. mRNA was extracted from the hybridoma cells, and cDNA was prepared by reverse transcription with reverse transcriptase. Mouse anti-glypican-3 heavy chain variable domain gene was amplified by PCR using the cDNA and a primer (CAGGGGCCAGTGGATAGACC-GATG) (SEQ ID NO: 1) having a nucleotide sequence complementary to mouse heavy chain variable domain gene, and obtained by ligating into pGEM-T easy (Promega). Human antibody heavy chain variable domain gene having homology to the framework regions of mouse anti-glypican-3 heavy chain variable domain gene was searched for and identified using Kabat database. The nucleotide sequence of a humanized anti-glypican-3 heavy chain variable domain gene, in which each framework portion of the identified human antibody heavy chain variable domain gene was ligated to each CDR portion of mouse anti-glypican-3 heavy chain variable domain, was designed and synthesized by PCR. The humanized anti-glypican-3 heavy chain variable domain gene was ligated to human IgG1 constant domain gene, followed by optimization through amino acid substitution. Thus, humanized anti-glypican-3 heavy chain gene was prepared (see WO06/06693). The heavy chain gene of humanized anti-human glypican-3 antibody was ligated downstream of CAG promoter, and mouse β globin polyA signal was ligated downstream of this heavy chain gene, to thereby prepare a heavy chain expression unit. It is possible to excise the heavy chain expression unit utilizing the BamHI and HindIII restriction sites upstream of the expression unit and the XhoI restriction site downstream of the expression unit.

Subsequently, the light chain gene of humanized anti-human glypican-3 antibody was prepared as described below. Briefly, mice were immunized with a glypican-3 fragment. Hybridoma cells were prepared using spleenocytes from these mice. Hybridoma cells were screened by ELISA using glypican-3 as antigen to thereby select those clones which produced glypican-3 binding antibodies. mRNA was extracted from the hybridoma cells, and cDNA was prepared by reverse transcription with reverse transcriptase. Mouse anti-glypican-3 light chain variable domain gene was amplified by PCR using the cDNA and a primer (GCTCACTGGATGGTGGGAAGATG) (SEQ ID NO: 2) having a nucleotide sequence complementary to mouse light chain variable domain gene, and obtained by ligation into pGEM-T Easy (Promega). Human antibody light chain variable domain gene having homology to the framework regions of mouse anti-glypican-3 light chain variable domain gene was searched for and identified using Kabat database. The nucleotide sequence of a humanized anti-glypican-3 light chain variable domain gene, in which each framework portion of the identified human antibody light chain variable domain gene was ligated to each CDR portion of mouse anti-glypican-3 light chain variable domain, was designed and synthesized by PCR. The humanized anti-glypican-3 light chain variable domain gene was ligated to human IgG κ constant domain gene, followed by optimization through amino acid substitution. Thus, humanized anti-glypican-3 light chain gene was prepared (see WO06/06693). The light chain gene of humanized anti-human glypican-3 antibody was ligated downstream of CAG promoter, and mouse β globin polyA signal was ligated downstream of this light chain gene, to thereby prepare a light chain expression unit. It is possible to excise the light chain expression unit with HindIII.

Plasmid INPEP4 (IDEC) digested with BamHI and XhoI and the heavy chain expression unit were ligated to thereby prepare pINP-GC33-H1. pINP-GC33-H1 digested with HindIII and the light chain expression unit excised with HindIII were ligated. By these operations, the following two plasmids were prepared: L-chain 1 copy expression plasmid phGC33CAG#1 retaining one copy of light chain expression unit and one copy of heavy chain expression unit per plasmid, and L-chain 2 copy expression plasmid phGC33CAG1 retaining two copies of light chain expression unit and one copy of heavy chain expression unit per plasmid (FIG. 1).

[Example 2] Preparation of Humanized Anti-Human Glypican-3 Antibody Stable Expression Cell Clones phGC33CAG#1 or phGC33CAG1 was introduced into CHO cell DXB11 strain by electroporation. Those cell clones which comprised the expression plasmid introduced thereinto were selected by culturing the cells in the presence of 400 μg/mL of G418. The selected clones were further cultured in the presence of 10-100 nM MTX for the purpose of gene amplification of the expression plasmid.

Figure 2:
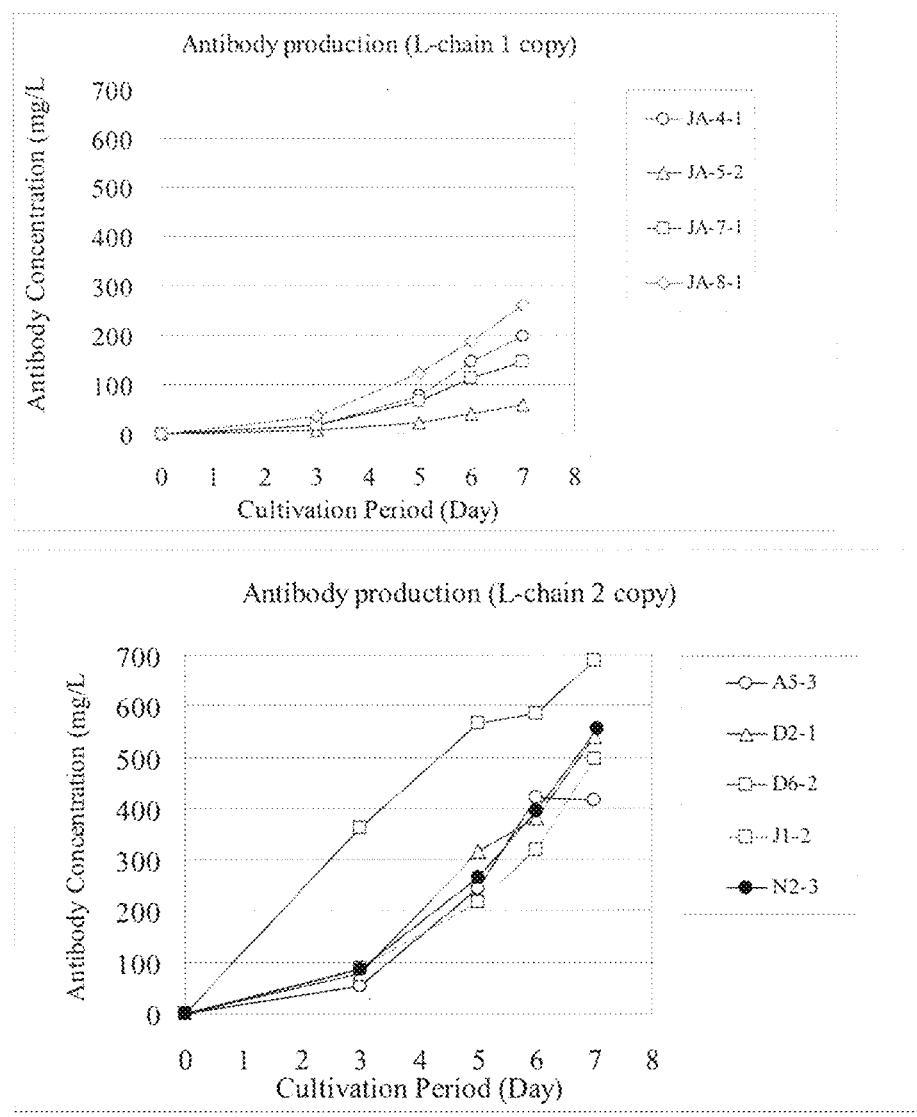
FIG. 2 is a graph showing productivity of the antibody (humanized anti-human glypican-3 antibody) by the "L-chain 1 copy expression plasmid"-transferred cell clone[s] and the "L-chain 2 copy expression plasmid"-transferred cell clone[s].

L-chain 1 copy expression plasmid-transformed cell clones (N=4) and L-chain 2 copy expression plasmid-transformed cell clones (N=5) were obtained. These clones were compared by batch culture in 125 mL flasks. The culture was performed under the following conditions: culture broth volume: 50 mL; initial cell density: $2 \times 10^5$ cells/mL; culture temperature: 37° C.; and shaking speed: 110 rpm. On days 3, 5, 6 and 7 of culture, antibody concentrations in the culture broth were measured and compared. Antibody yield on day 7 was about 60-260 μg/mL in L-chain 1 copy expression plasmid-transformed cell clones (N=4). On the other hand, antibody yield on day 7 was about 420-690 μg/mL in L-chain 2 copy expression plasmid-transformed cell clones (N=5). The antibody yield of L-chain 2 copy expression plasmid-transformed cell clones was more than twice as high as that of L-chain 1 copy expression plasmid-transformed cell clones (FIG. 2).

From the above results, it was confirmed that antibody yield can be enhanced by introducing into a host cell the heavy chain and light chain genes at a heavy chain:light chain gene ratio of 1:2, as opposed to the ratio of 1:1 used in conventional processes.

Figure 3:
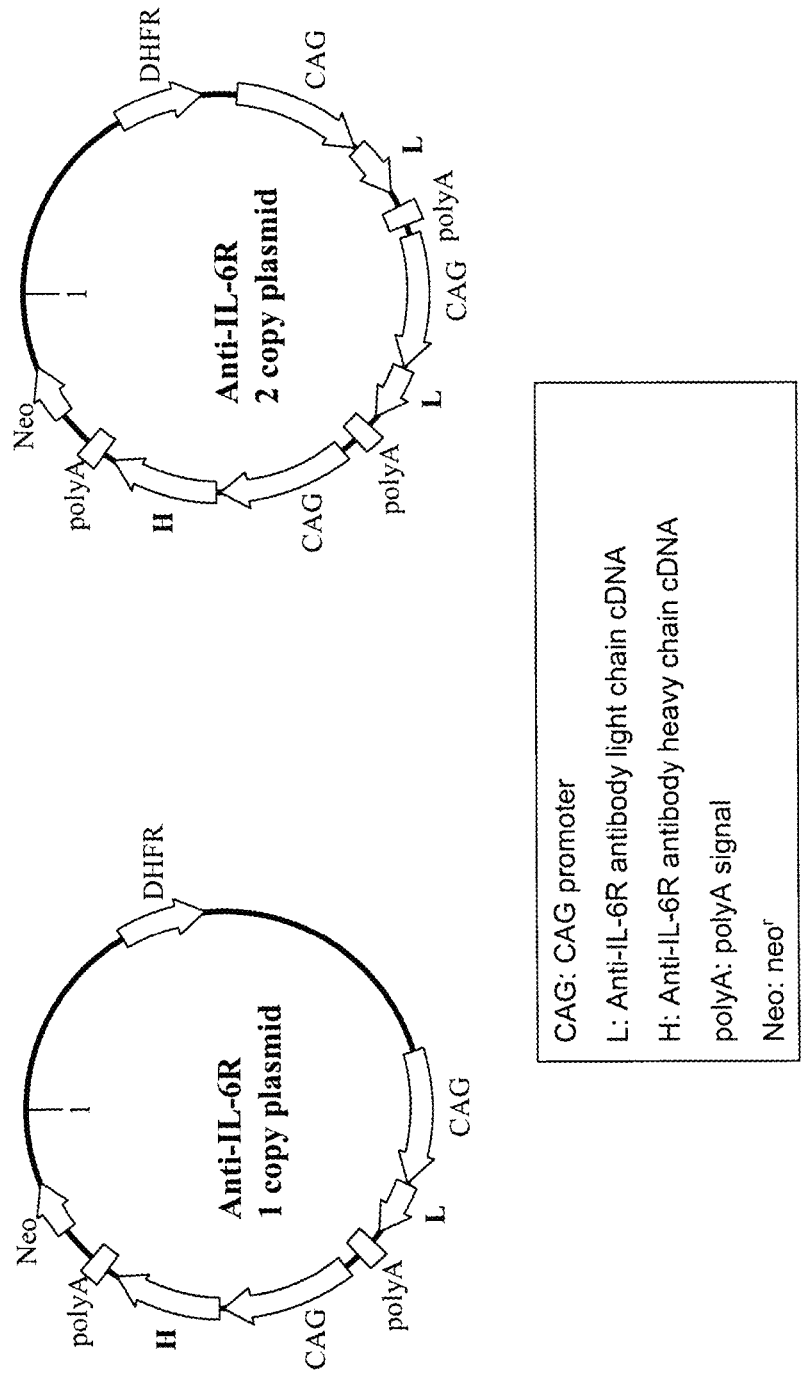
FIG. 3 shows "L-chain 1 copy expression plasmid" comprising one copy of the heavy chain of humanized anti-human IL-6R antibody gene and one copy of the light chain of the gene, and "L-chain 2 copy expression plasmid" comprising one copy of the heavy chain and two copies of the light chain.

[Example 3] Preparation of Humanized Anti-Human IL-6R Antibody Stable Expression Cell Clones CAG promoters were ligated upstream of humanized anti-human IL-6R antibody heavy chain gene and humanized anti-human IL-6R antibody light chain gene (both disclosed in WO92/019759), respectively. Subsequently, mouse β globin polyA signals were ligated downstream of the two genes, respectively. Thus, a heavy chain expression unit and a light chain expression unit were prepared. The heavy chain expression unit and the light chain expression unit were ligated to pBluescript integrating neomycin resistance gene and dhfr; as a result, an L-chain 1 copy expression plasmid composed of one copy of the heavy chain of humanized anti-human IL-6R antibody gene and one copy of the light chain and an L-chain 2 copy expression plasmid composed of one copy of the heavy chain and two copies of the light chain were prepared (FIG. 3). These plasmids were introduced into CHO cell DXB11 strain by electroporation. Those cell clones which comprised the expression plasmid introduced thereinto were selected by subsequently culturing the cells in the presence of 400 μg/mL of G418.

Figure 4:
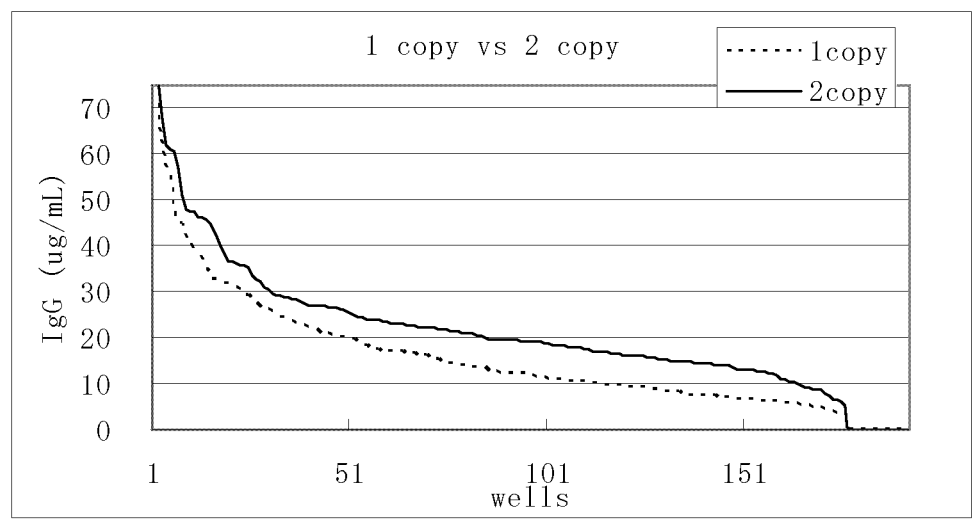
FIG. 4 is a graph showing productivity of the antibody (humanized anti-human IL-6R antibody) by the "L-chain 1 copy expression plasmid"-transferred cell clone[s] and the "L-chain 2 copy expression plasmid"-transferred cell clone[s].
Figure 4:
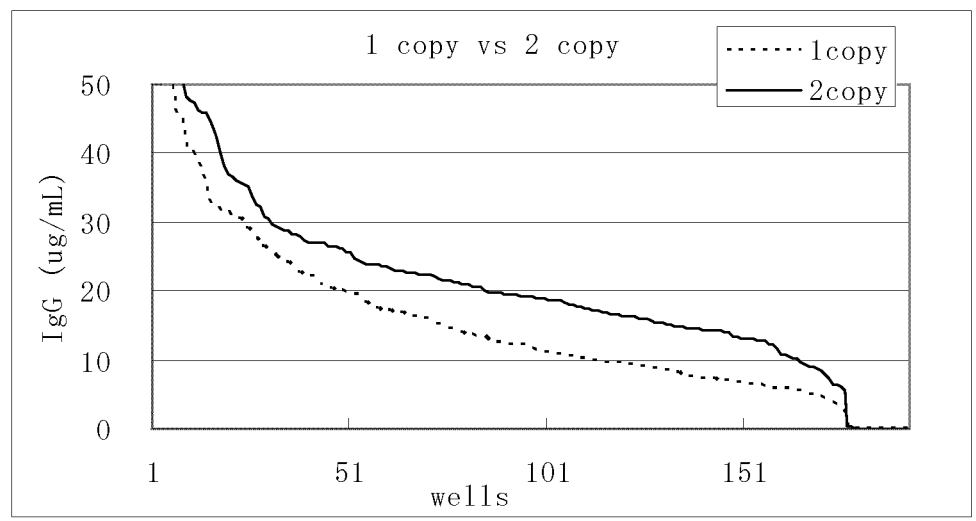

L-chain 1 copy expression plasmid-transformed cell clones (N=176) and L-chain 2 copy expression plasmid-transformed cell clones (N=176) were obtained. These clones were compared by batch culture in 24-well plates. The culture was performed under the following conditions: culture broth volume: 0.7 mL; culture temperature: 37° C.;

and shaking speed: 160 rpm. On day 12 of culture, antibody concentrations in the culture broth were measured. After clones were arranged by antibody yield, the two groups of clones were compared (FIG. 4). Generally, the antibody yield of L-chain 2 copy expression plasmid-transformed cells was higher than that of L-chain 1 copy expression plasmid-transformed cells.

From the above results, it was confirmed that antibody yield can be enhanced by introducing into a host cell the heavy chain and light chain genes at a heavy chain:light chain gene ratio of 1:2, as opposed to the ratio of 1:1 used in conventional processes.

The present invention is applicable to all antibody-producing cells.

All publications, patents and patent applications cited herein are incorporated herein by reference in their entirety.

INDUSTRIAL APPLICABILITY

The present invention is applicable to antibody production.

SEQUENCE LISTING FREE TEXT

<SEQ ID NO: 1>

SEQ ID NO: 1 shows the sequence of a primer having a nucleotide sequence complementary to mouse heavy chain variable domain gene.

SEQ ID NO: 2 shows the sequence of a primer having a nucleotide sequence complementary to mouse light chain variable domain gene.

The invention claimed is:

1. A method of producing an IgG1 antibody or an antigen binding fragment thereof, comprising allowing a cell to produce the antibody or the antigen binding fragment thereof, wherein the cell contains a larger number of copies of an exogenous DNA encoding the light chain or an antigen binding fragment thereof of the antibody than the number of copies contained in the cell of an exogenous DNA encoding the heavy chain or an antigen binding fragment thereof of the antibody.

2. The method according to claim 1, wherein a vector comprising one copy of a DNA encoding the heavy chain or an antigen binding fragment thereof of the antibody and two or more copies of a DA encoding the light chain or an antigen binding fragment thereof of the antibody have been introduced into the cell.

3. The method according to claim 1, wherein the cell is an animal cell.

4. The method according to claim 3, wherein the cell is Chinese hamster ovary cell.

5. The method according to claim 1, wherein the antibody is a chimeric antibody, humanized antibody or human antibody.

6. The method according to claim 1, wherein the antibody is selected from the group consisting of anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody and anti-VLA4 antibody.

7. The method of manufacturing a pharmaceutical, comprising preparing an antibody or an antigen binding fragment thereof according to claim 1 and combining the antibody or an antigen binding fragment thereof with a pharmaceutically acceptable carrier.

8. A recombinant expression vector comprising a larger number of copies of a DNA encoding the light chain or an antigen binding fragment thereof of IgG1 antibody and two or more copies of a DNA encoding the heavy chain or an antigen binding fragment thereof of the antibody.

9. A recombinant expression vector according to claim 8 which comprises one copy of a DNA encoding the heavy chain or an antigen binding fragment thereof of an IgG1 antibody and two or more copies of a DNA coding the light chain or an antigen binding fragment thereof of the antibody.

10. A cell comprising the vector according to claim 8.

11. A method of producing an IgG1 antibody or an antigen binding fragment thereof, comprising culturing a cell to produce the antibody or the antigen binding fragment thereof, wherein the cell expresses a light chain of the antibody or an antigen binding fragment thereof in a higher yield than a heavy chain of the antibody of an antigen binding thereof, wherein the vector comprising one copy of a DNA encoding the heavy chain or an antigen binding fragment thereof of the antibody and two copies of a DNA encoding the light chain or an antigen binding fragment thereof of the antibody have been introduced into the cell.

12. The method according to claim 1, wherein the cell is stably expressing the antibody or the antigen binding fragment thereof.

13. The cell according to claim 9, which is stably expressing the antibody or the antigen binding fragment thereof.

\* \* \* \* \*

SEQUENCE LISTING

<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
caggggccag tggatagacc gatg                        24

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
gctcactgga tggtgggaag atg                         23